United States Patent [19]

Zaiger

[11] Plant 5,138

[45] Nov. 15, 1983

[54] APRICOT TREE (SPRING GIANT)

[76] Inventor: C. Floyd Zaiger, 537 Rosemore Ave., Modesto, Calif. 95351

[21] Appl. No.: 366,158

[22] Filed: Apr. 7, 1982

[51] Int. Cl.[3] ..... A01H 5/03
[52] U.S. Cl. ..... Plt./39
[58] Field of Search ..... Plt./39

*Primary Examiner*—Robert E. Bagwill

[57] ABSTRACT

A new and distinct variety of apricot tree of large size, medium dense, upright in growth and the tree being a regular and productive bearer of very large size, firm, yellow flesh, freestone fruit; the fruit is further characterized by excellent eating quality and its ability to ship to long distance markets.

1 Drawing Figure

ORIGIN OF THE VARIETY

The new variety of apricot tree was originated by me in my experimental orchard, located near Modesto, Calif. as a first generation seedling from a cross between King Cot Apricot (Non-patented) and an apricot seedling of the parentage, (Flaming Gold Apricot (U.S. Plant Pat. No. 2,822)×Gold Kist Apricot (U.S. Plant Pat. No. 2,826)). The seedlings from this cross were planted and grown under careful observation by me; one such seedling which is the present variety having been especially desirable with respect to the fruit, was selected for asexual reproduction and commercialization.

ASEXUAL REPRODUCTION OF THE VARIETY

The present variety of apricot tree was asexually reproduced by budding in my experimental orchard near Modesto, Calif. and shows that all characteristics come true to form and are established and transmitted through succeeding propagations.

SUMMARY OF THE VARIETY

The new and distinct variety of apricot tree is of large size, medium dense and upright in growth and a regular and productive bearer of very large size, firm, yellow flesh, freestone fruit with excellent eating quality. The fruit is further characterized by early maturity and having the ability to ship to long distance markets. The present variety of apricot tree when compared to Flaming Gold Apricot (U.S. Plant Pat. No. 2,822), bears larger fruit, has a more even and uniform ripening of the fruit throughout the tree and matures 4 to 5 days later.

PHOTOGRAPHS OF THE VARIETY

The accompanying photographs show typical specimens of the fruit and foliage of my new variety of apricot tree and a section of a small branch with the upper and lower surfaces of the foliage being illustrated. An exterior view of the fruit is shown with a fruit divided on its suture plane to reveal flesh coloration and showing a stone remaining in place. The photographs were taken shortly after being picked at maturity (shipping ripe), and the colors are as nearly true as reasonably possible in a color presentation of this type.

DESCRIPTION OF THE VARIETY

The following is a detailed description of the new variety of apricot tree and its flowers, foliage and fruit based on observations of specimens grown at Modesto, Calif., with color terminology in accordance with Reinhold Color Atlas by A. Korneruf and J. H. Wanscher.

Tree:
- *Size.*—Large.
- *Vigor.*—Vigorous.
- *Growth.*—Upright.
- *Density.*—Medium dense.
- *Production.*—Productive.
- *Bearing.*—Regular.

Trunk:
- *Size.*—Stocky.
- *Surface.*—Shaggy.

Branches:
- *Size.*—Medium stocky.
- *Lenticels.*—Medium size. Medium number.
- *Texture.*—Smooth to medium rough.
- *Color.*—Dark brown — (8-F-6) to (8-F-8). Reddish brown — (9-E-6) to (9-E-8).

Leaves:
- *Size.*—Large. Average length — 3" to $3\frac{3}{4}$". Average width — $2\frac{3}{4}$" to $3\frac{1}{2}$".
- *Shape.*—Ovate to orbicular, pointed.
- *Petiole.*—Medium length. Medium thickness.
- *Glands.*—Number one to six. Average 2.
- *Margin.*—Serrate.
- *Color.*—Upper surface — (28-E-6) to (28-E-8). Lower surface — (28-D-5) to (28-D-6).

Flower buds:
- *Size.*—Medium.
- *Length.*—Medium, plump.

Flowers:
- *Blooming period.*—First bloom — Feb. 23, 1981. Full bloom — Feb. 28, 1981.
- *Size.*—Large.
- *Color.*—Varies from white to light pink.
- *Pubescense.*—Present.

Fruit:
- *Maturity when described.*—Shipping ripe.
- *Date of first picking.*—May 29, 1981.
- *Date of last picking.*—June 2, 1981.
- *Size.*—Comparatively uniform. Very large. Average diameter axially — $2\frac{1}{4}$" to $2\frac{3}{4}$". Average diameter transversely in suture plane — $2\frac{1}{4}$" to $2\frac{3}{4}$". Average diameter measured at right angles to suture plane 2" to $2\frac{1}{2}$".
- *Form.*—Slightly variable, globose, somewhat compressed laterally toward suture.

*Suture.*—Usually pronounced from stem to blossom end, slightly deeper near blossom end.

*Cavity.*—From rounded to slightly elongated in suture plane. Average depth — $\frac{1}{4}''$. Average breadth — $\frac{1}{2}''$.

*Base.*—Rounded to slightly retuse.

*Apex.*—Rounded, pistil point slightly depressed.

Skin:

*Thickness.*—Thin to medium.

*Texture.*—Moderately smooth.

*Tendency to crack.*—None.

*Down.*—Scant, very short.

*Color.*—Apricot yellow — (5-B-7) to (5-B-8) to reddish orange — (7-B-7) to (7-B-8) on position of fruit exposed to sun.

Flesh:

*Ripens.*—Fairly uniform, only slightly earlier at apex.

*Texture.*—Firm, fine melting.

*Fibers.*—Medium size, tender.

*Flavor.*—Mild.

*Eating quality.*—Excellent.

*Color.*—Golden yellow — (5-B-8) to light orange — (6-B-8).

Stone:

*Type.*—Free; adheres to flesh somewhat along ventrical edge.

*Size.*—Large. Average length — $1\frac{1}{4}''$. Average breadth — $1\frac{1}{8}''$. Average thickness — $\frac{5}{8}''$.

*Form.*—Ovoid.

*Base.*—Straight.

*Apex.*—Nearly rounded.

*Surface.*—Pitted, slightly deeper toward apex.

*Ridges.*—Two distinct ridges extending approximately 180° across the surface on both sides of the suture plane and approximately 35° displaced from each other.

*Color.*—Varies slightly, from light brown — (6-C-6) to brown (6-D-6).

*Tendency to split.*—None.

Use: Canning, drying, local and long distance markets.

Keeping quality: Very good.

Shipping quality: Good.

The apricot tree and its fruit herein described may vary in slight detail due to climatic and soil conditions under which it may be grown; the description is that of the variety grown under ecological conditions at Modesto, Calif.

The following is claimed:

1. A new and distinct variety of apricot tree of large size, vigorous upright growth and a regular and productive bearer of very large, firm yellow flesh, freestone fruit with excellent eating quality and the ability to ship to long distance markets; the apricot tree is further characterized when compared to the Flaming Gold Apricot Tree (U.S. Plant Pat. No. 2,822) as having a more uniform distribution of fruit within the center of the tree and a more uniform ripening of the fruit throughout the tree.

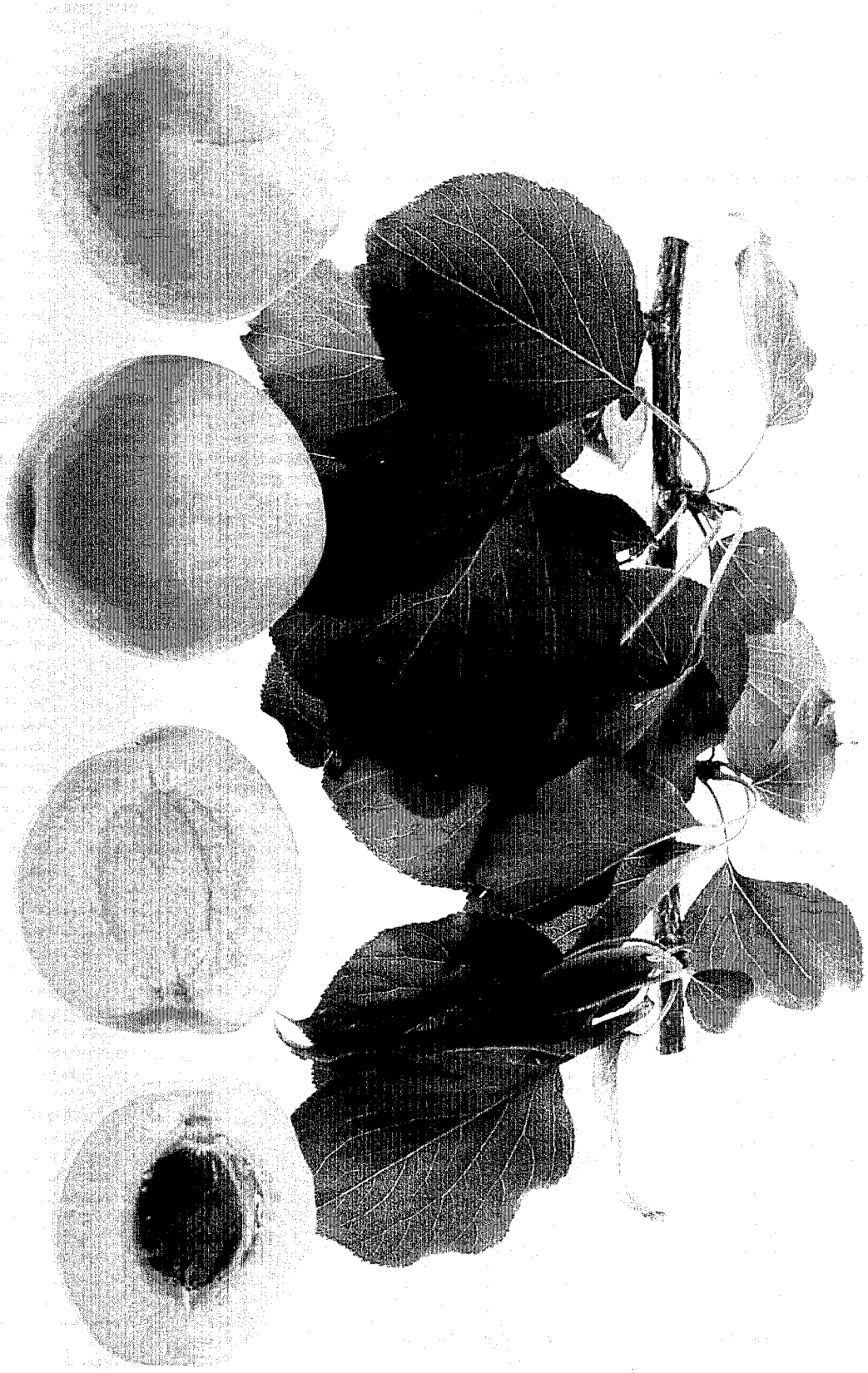

* * * * *